(12) United States Patent
Thaxton et al.

(10) Patent No.: US 7,807,393 B2
(45) Date of Patent: Oct. 5, 2010

(54) BIOMARKERS FOR PROSTATE CANCER

(75) Inventors: Colby Shad Thaxton, Chicago, IL (US);
Norm D. Smith, Chicago, IL (US);
Joseph Pazona, Chicago, IL (US);
Onisuru T. Okotie, Oak Park, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 12/021,909

(22) Filed: Jan. 29, 2008

(65) Prior Publication Data

US 2008/0181850 A1    Jul. 31, 2008

Related U.S. Application Data

(60) Provisional application No. 60/897,954, filed on Jan. 29, 2007.

(51) Int. Cl.
*G01N 33/574* (2006.01)
(52) U.S. Cl. ........................ 435/7.23; 435/7.1
(58) Field of Classification Search ........... None
See application file for complete search history.

(56) References Cited

U.S. PATENT DOCUMENTS

2002/0168713 A1* 11/2002 Curtis ................. 435/69.1

OTHER PUBLICATIONS

IHOP entry for the NLGN4Y polypeptide, May 27, 2009.*
Epstein and Potter, "The pathological interpretation and significance of prostate needle biopsy findings: implications and current controversies" 2001, J. Urol., 166:402.
Etzioni et al., 1999, J. Natl. Cancer Inst., 91:1033.
Gleason, "Classification of prostatic carcinomas" 1966, Cancer Chemother. Rep. 50:125.
Gleason, "Histologic grading of prostate cancer: a perspective" 1992, Hum. Pathol. 23:273.
Jacobsen et al., "Incidence of prostate cancer diagnosis in the eras before and after serum prostate-specific antigen testing" 1995 JAMA 274:1445.
Jamain et al., "Neuroligin 2 is exclusively localized to inhibitory synapses" 2004 Eur J Cell Biol. 83(9):449-56.
Maattanen et al., "European randomized study of prostate cancer screening: first-year results of the Finnish trial" 1999 Br. J. Cancer 79:1210.
Negase et al., "Prediction of the coding sequences of unidentified human genes XI11 the complete sequences of 100 new cDNA clones from brain which code for large proteins in vitro" 1999, DNA Res. 6:63-70.
Schroder et al., "Evaluation of the digital rectal examination as a screening test for prostate cancer. Rotterdam section of the European Randomized Study of Screening for Prostate Cancer" 1998 J. Natl. Cancer Inst., 90:1817.
Skaletsky et al., "The male-specific region of the human Y chromosome is a mosaic of discrete sequence classes" 2003, Nature 423:825-837.

* cited by examiner

*Primary Examiner*—Misook Yu
*Assistant Examiner*—Mark Halvorson
(74) *Attorney, Agent, or Firm*—Casimir Jones, S.C.

(57) ABSTRACT

The present invention relates to compositions and methods for the detecting, treating, and empirically investigating the prostate. In particular, the present invention provides compositions and methods for using neuroligin biomarkers (e.g., NLGN-4Y) in the diagnosis, treatment, and empirical investigation of prostate disorders (e.g., prostate cancer, benign prostatic hypertrophy).

9 Claims, 5 Drawing Sheets

Figure 3.
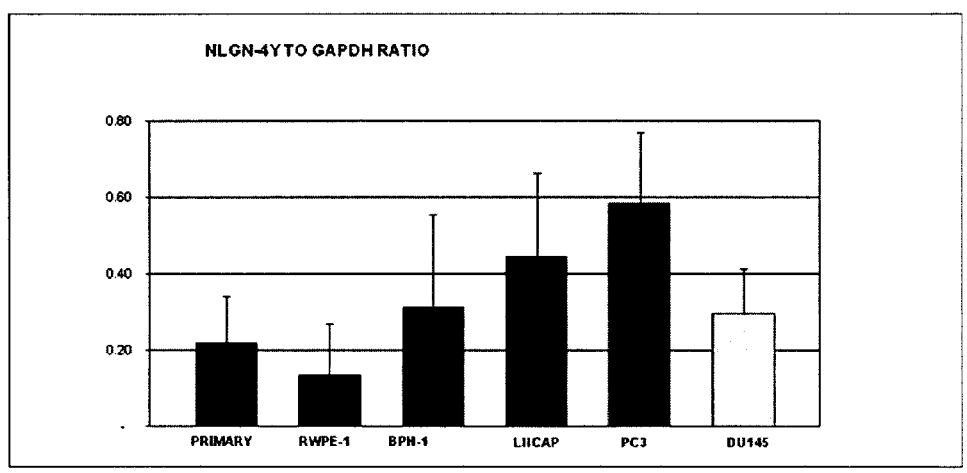

FIGURE 4
| BPH | Prostate Cancer |
|---|---|
| 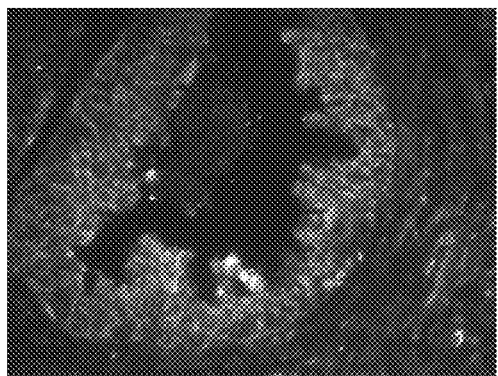 | 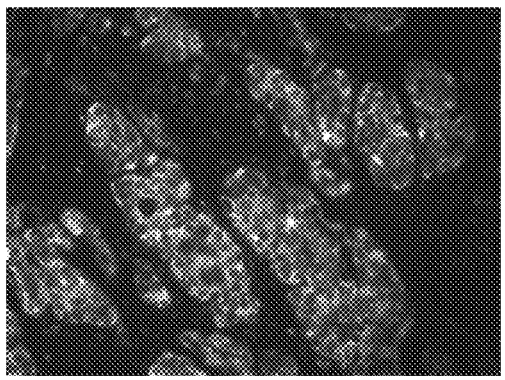 |
| 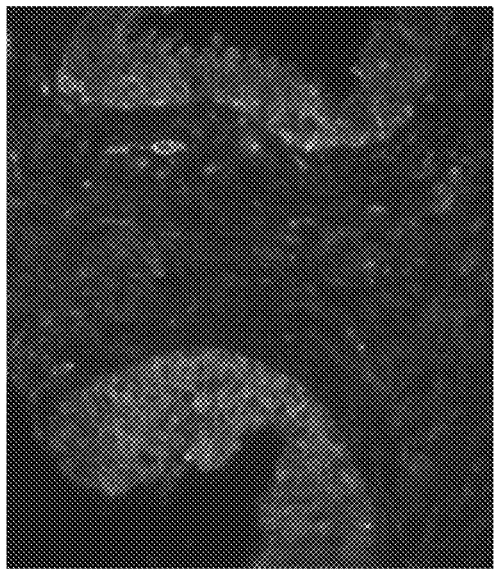 | 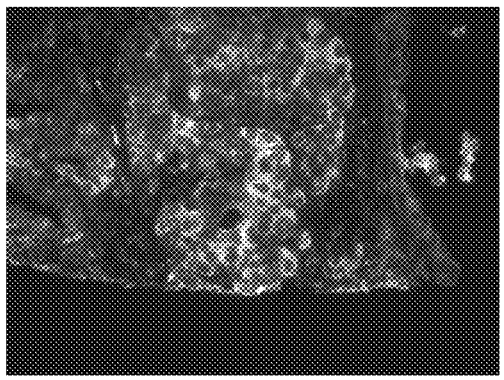 |

BIOMARKERS FOR PROSTATE CANCER

The present application claims priority to U.S. Provisional Patent Application Ser. No. 60/897,954, filed Jan. 29, 2007, which is herein incorporated by reference in its entirety.

FIELD OF THE INVENTION

The present invention relates to compositions and methods for the detecting, treating, and empirically investigating prostate cancer. In particular, the present invention provides compositions and methods for using neuroligin biomarkers (e.g., NLGN-4Y) in the diagnosis, treatment, and empirical investigation of prostate disorders (e.g., prostate cancer, benign prostatic hypertrophy).

BACKGROUND OF THE INVENTION

Afflicting one out of nine men over age 65, prostate cancer (PCA) is a leading cause of male cancer-related death, second only to lung cancer (Abate-Shen and Shen, 2000, Genes Dev 14:2410; Ruijter et al., 1999, Endocr Rev, 20:22). Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise suspicions that a patient has prostate cancer, while amounts above 50 may show that the tumor has spread elsewhere in the body.

Biopsies of various sectors of the prostate are used to determine if prostate cancer is present. Treatment options depend on the stage of the cancer. Men with a 10-year life expectancy or less who have a low Gleason number and whose tumor has not spread beyond the prostate are often treated with watchful waiting (no treatment). Treatment options for more aggressive cancers include surgical treatments such as radical prostatectomy (RP), in which the prostate is completely removed (with or without nerve sparing techniques) and radiation, applied through an external beam that directs the dose to the prostate from outside the body or via low-dose radioactive seeds that are implanted within the prostate to kill cancer cells locally. Anti-androgen hormone therapy is also used, alone or in conjunction with surgery or radiation. Hormone therapy uses luteinizing hormone-releasing hormones (LH-RH) analogs, which block the pituitary from producing hormones that stimulate testosterone production. Patients must have injections of LH-RH analogs for the rest of their lives.

While surgical and hormonal treatments are often effective for localized PCA, advanced disease remains essentially incurable. Androgen ablation is the most common therapy for advanced PCA, leading to massive apoptosis of androgen-dependent malignant cells and temporary tumor regression. In most cases, however, the tumor reemerges with a vengeance and can proliferate independent of androgen signals.

The advent of prostate specific antigen (PSA) screening has led to earlier detection of PCA and significantly reduced PCA-associated fatalities. However, the impact of PSA screening on cancer-specific mortality is still unknown pending the results of prospective randomized screening studies (Etzioni et al., 1999, J. Natl. Cancer Inst., 91:1033; Maattanen et al., 1999, Br. J. Cancer 79:1210; Schroder et al., 1998, J. Natl. Cancer Inst., 90:1817). A major limitation of the serum PSA test is a lack of prostate cancer sensitivity and specificity especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., 1995, JAMA 274:1445). This has resulted in a surge of equivocal prostate needle biopsies (Epstein and Potter, 2001, J. Urol., 166:402).

As such, what are needed are the identification of additional biomarkers for use in the diagnosis, treatment, and fundamental research of prostatic cancers.

SUMMARY OF THE INVENTION

The present invention relates to compositions and methods for cancer diagnostics, including but not limited to, cancer markers. In particular, the present invention provides neuroligin biomarkers useful for the screening, diagnosis, characterization, and treatment of prostate cancers and other prostate diseases.

Currently, prostate specific antigen (PSA) serves as the gold standard serum biomarker used for prostate cancer screening. As such, PSA screening has come under intense scrutiny, mostly due to a lack of specificity that elevated PSA levels have for a prostate cancer diagnosis. Elevated PSA serum levels can also signify the presence of prostate inflammation and benign prostate enlargement. In fact, when progressively higher-grade (more aggressive) prostate cancer tissue specimens are interrogated for PSA expression, an inverse correlation is observed such that higher-grade specimens stain less intensely for PSA expression. This is troubling clinically in that the prostate cancers that pose the greatest risk to the patient are those that are high grade. In order to better identify those prostate cancers that have more aggressive potential there has been a lot of effort to identify biomarkers that are more likely to be found in higher-grade prostate cancer.

In one embodiment, the present invention provides methods of detecting prostate cancer in a subject. In some embodiments, the methods detect prostate cancer in a subject using a sample, for example a tissue, blood, blood product (e.g., plasma, serum) or bodily fluid (e.g., urine, CSF). In some embodiments, detecting prostate cancer comprises detecting a neuroligin in a sample. In some embodiments, the methods of the present invention comprise the detecting of the neuroligin NLGN-4Y in a sample. NLGN-4Y, also known as KIAA0951 (OMIM400028) comprises the protein sequence as found in Genbank Accession No. NM_055708, and nucleic acid sequence NM_014893. However, fragments, protein precursors, and isoforms of NLGN-4Y find utility, are contemplated for use in the present invention and are described in, for example, Genbank Accession Nos. AAI13526, AAI13552, AAH32567, Q8NFZ3, EAW91625, EAW91624, EAW91623, EAW91622, EAW91621, EAQ91620. In some embodiments, detecting the neuroligin comprises the detection of the neuroligin protein NLGN-4Y or fragments, precursors, and isoforms thereof. In some embodiments, detecting the neuroligin comprises detecting neuroligin nucleic acids (e.g., DNA, mRNA).

In one embodiment, the present invention provides methods of detecting or diagnosing prostate cancer in a subject. In some embodiments, the methods of detecting or diagnosing prostate cancer in a subject comprises detecting the presence or absence of a neuroligin in a sample. In some embodiments, a sample is, for example a tissue, blood, blood product (e.g., plasma, serum) or bodily fluid (e.g., expressed prostatic secretion, urine, CSF). In some embodiments, detecting the presence of NLGN-4Y protein (or fragments, protein precursors, and isoforms thereof) or nucleic acid in a sample is indicative of prostate cancer. In some embodiments, diagnosing prostate cancer in a subject comprises diagnosing the type of prostate cancer (e.g., benign prostatic hyperplasia, prostatic intraepithelial neoplasia, prostate cancer) in a subject based the level of expression of a neuroligin (e.g. NLGN-4Y) protein (or fragments, protein precursors, and isoforms thereof) or nucleic acid in a sample.

In some embodiments, the present invention provides methods for determining the risk of a subject in developing prostate cancer. In some embodiments, the methods comprise detecting the amount of a neuroligin (e.g., NLGN-4Y) protein (or fragments, protein precursors, and isoforms thereof) or nucleic acid in a subject sample (e.g., tissue, blood, blood component, urine, etc.) and correlating the presence of, absence of, or amount of neurologin with the risk of prostate cancer development. In some embodiments, the risk comprises the risk of a subject developing prostate cancer, or the risk of a subject currently diagnosed with prostate cancer progressing to a more advanced stage of prostate cancer. Even where a risk profile is not absolute, assessment of risk, alone or in combination with risk factors (e.g., age, other biomarkers) provides treating physicians with useful information for managing patient care, including but not limited to, initiating therapy, biopsy, other diagnostics, watchful waiting, and the like.

In some embodiments, the methods of the present invention are used in conjunction with other methods for diagnosing prostate cancer in a subject. Such methods include, but are not limited to, the determination of other prostate cancer biomarkers such as PSA.

In some embodiments, the methods of the present invention comprise communicating to the subject suspected of having prostate cancer, or a subject undergoing prostate cancer treatment, a disease prognosis. In some embodiments, the prognosis comprises detecting the presence or absence of a neuroligan (e.g., NLGN-4Y) in a subject's sample, and correlating the result with the presence, and levels thereof, of a neuroligan present in said sample, wherein the presence of an increased amount of neuroligin present is indicative of a more aggressive cancer, and the presence of less neuroligan present in a sample is indicative of a less aggressive cancer. Tables 1-3 are exemplary in demonstrating the correlation in expression of the neuroligan NLGN-4Y and the degree of prostate cancer stage.

In one embodiment, the present invention provides kits for assaying for inhibitors or prostate cancer. In some embodiments, inhibitors of prostate cancer include, but are not limited to, test compounds such as small molecules, drugs, and RNAi (e.g., siRNA, dsRNA). In some embodiments, the kits find use in assaying for inhibitors in vitro, for example, in cell lysates and tissue culture systems. In some embodiments, the kits find use in assaying for inhibitors in vivo, for example in a non-human subject and a human subject. In some embodiments, the methods of the kits comprise applying a compound that may inhibit prostate cancer to a sample or subject, and evaluating the effect of that compound on the expression of a neuroligin, for example, NLGN-4Y, in the sample or subject. Expression evaluation is performed, for example, by comparing the protein and/or nucleic acid expression of NLGN-4Y before the application of a test compound to protein and/or nucleic acid expression after application of a test compound.

BRIEF DESCRIPTION OF THE DRAWINGS

FIG. 3 shows a Western Blot demonstrating NLGN-4Y differential expression in a normal prostate cell line, BPH cell line, and prostate cancer cell lines.

FIG. 4 shows immunofluorescence staining of NLGN-4Y in BPH and prostate cancer tissue.

DEFINITIONS

Figure 1:
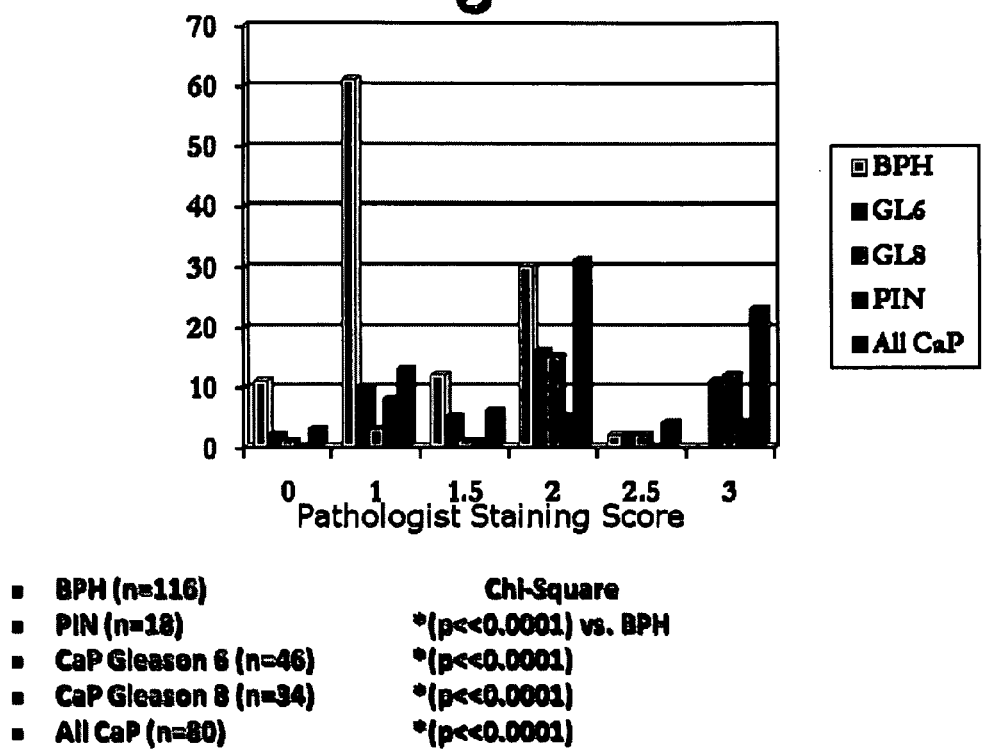
FIG. 1 shows the staining (range of 0-3; 0=no staining, 3=strong staining) of the prostate tissue for NLGN-4Y.

The term "epitope" as used herein refers to that portion of an antigen that makes contact with a particular antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass or increased PSA level) but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "characterizing prostate tissue in a subject" refers to the identification of one or more properties of a prostate tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient. Cancer marker expression may be characterized using any suitable method.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous prostate control" refers to measuring the level of expression of a gene (e.g., the level of mRNA or protein) relative to the level in a non-cancerous prostate control sample. Gene expression can be measured using any suitable method, including but not limited to, those described herein.

As used herein, the term "detecting a change in gene expression (e.g., NLGN gene such as NLGN-4Y) in said prostate cell sample in the presence of said test compound relative to the absence of said test compound" refers to measuring an altered level of expression (e.g., increased or decreased) in the presence of a test compound relative to the absence of the test compound. Gene expression can be measured using any suitable method.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "post surgical tumor tissue" refers to cancerous tissue (e.g., prostate tissue) that has been removed from a subject (e.g., during surgery).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to results of initial cancer diagnosis (e.g., the presence or absence of cancerous cells). An initial diagnosis does not include information about the stage of the cancer of the risk of prostate specific antigen failure.

As used herein, the term "biopsy tissue" refers to a sample of tissue (e.g., prostate tissue) that is removed from a subject for the purpose of determining if the sample contains cancerous tissue. In some embodiment, biopsy tissue is obtained because a subject is suspected of having cancer. The biopsy tissue is then examined (e.g., by microscopy) for the presence or absence of cancer.

As used herein, the term "inconclusive biopsy tissue" refers to biopsy tissue for which histological examination has not determined the presence or absence of cancer.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid. A fragment of a protein may have activity of the native protein, or it may not.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source. Biological samples may be obtained from animals (including humans) and encompass fluids, solids, and tissues. Biological samples include blood products, such as plasma, serum, whole blood and the like. Biological samples also include tissue samples, such as biopsy tissues or pathological tissues that had previously been fixed (e.g., formalin, cytological processing, etc.).

DETAILED DESCRIPTION OF THE INVENTION

Exemplary compositions and methods of the present invention are described in more detail in the following sections: I. Neuroligin Biomarkers; II. Detection of Prostate Disorders; III. In vivo Imaging; IV. Antibodies; V. Therapeutics; VI. Drug Screening; and VII. Kits.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is incorporated herein by reference in their entireties.

I. Neuroligin Biomarkers

The neuroligins (NLGNs), in particular, NLGN-4Y are identified herein as biomarkers for prostate cancers. Neurolignins are cells adhesion molecules present at the postsynaptic side of the synapse, and may be essential for the formation of functional synapses (Jamain et al., 2003, Nat, Genet. 34:27-29, incorporated herein by reference in its entirety). The NLGN designated Y-linked NLGN-4Y gene maps to chromosome Yq11.2. Nagase et al. (1999, DNA Res. 6:63-70, incorporated herein by reference in its entirety) cloned NLGN-4Y, and found that the 648 amino acid protein shares 77.5% homology with the rat NLGN2 protein. NLGN-4Y expression was found in nearly all tissues examined by Nagase et al. Jamain et al. (2004) determined that all amino acids essential for neuroligins are conserved in NLGN-4Y and its X-linked homolog NLGN4, including the cysteines, transmembrane domain, and PDZ binding domain. RT-PCR detected similar expression of NLGN4 and NLGN-4Y is all male brain regions examined, while only NLGN4 was expressed in female brain regions. Skaletsky et al., (2003, Nature 423:825-837, incorporated herein by reference in its entirety) determined that NLGN-4Y was expressed in fetal and adult brain, prostate, and testis (Genbank Accession No. NP_055708 (amino acid) and NM_014893 (nucleic acid), incorporated herein by reference in their entireties). The present invention provides for the use of a neuroligin, in particular NLGN-4Y protein (or fragments, protein precursors, and isoforms thereof) or nucleic acid, as a biomarker for the detection, diagnosis and treatment of prostate cancer.

Experiments performed while developing embodiments of the present invention demonstrate that NLGN-4Y is expressed more strongly in higher-grade prostate cancers as opposed to benign disease, and that there is a linear relationship between increased grade (e.g., more aggressive potential of the tumor) and NLGN-4Y amount. As such, NLGN-4Y also finds utility in identifying subjects with different types/stages of prostate cancer, as well as delineate aggressive cancers from non-aggressive cancers. Such identification and delineation allows a clinician to treat the subject in a more rational manner based on the diagnosis. For example, in some embodiments the identification of a patient at risk of developing prostate cancer or a subject with a non-aggressive cancer allows a clinician to apply different treatment regimens, if any are applied at all. In some embodiments, identifying a subject with a more aggressive form of prostate cancer allows a clinician to pursue a more aggressive treatment regimen.

Accordingly, the present invention provides compositions and methods for using neuroligin biomarkers (e.g., NLGN-4Y) in the diagnosis, treatment, and empirical investigation of prostate disorders (e.g., prostate cancer, benign prostatic hypertrophy). The present invention also provides methods for distinguishing between benign prostatic hyperplasia (BPH) and prostate cancer (PCa) through measuring neuroligin biomarker (e.g., NLGN-4Y) serum levels in subjects.

II. Detection of Prostate Disorders

The present invention provides methods of detecting prostate disorders (e.g., BPH, prostatic intraepithelial neoplasi (PIN), localized prostate cancer (PCa), metastatic prostate cancer (metPCa), etc.) comprising detecting and quantifying specific neuroligin (e.g., NLGN-4Y) expression.

In some embodiments, the present invention provides methods for detecting expression of neuroligin biomarkers (e.g., NLGN-4Y). In some embodiments, expression is measured directly (e.g., at the nucleic acid or protein level). In some embodiments, expression is detected in tissue samples (e.g., biopsy tumor tissue). In other embodiments, expression is detected in bodily fluids (e.g., including but not limited to, plasma, serum, CSF, whole blood, mucus, expressed prostatic secretion, and urine). The present invention further provides panels and kits for the detection of neuroligin biomarkers (e.g., NLGN-4Y). In preferred embodiments, the presence of a neuroligin biomarker (e.g., NLGN-4Y) is used to provide a prognosis to a subject. For example, detection of NLGN-4Y expression in tissues (e.g., prostate tissue) above or below a certain threshold level may be indicative of a prostate disorder (e.g., prostate cancer, BPH).

In some embodiments, detection of the presence or absence of a prostate disorder or the characterization of a prostate disorder is accomplished through comparing expression levels of neuroligin biomarkers (e.g., NLGN-4Y) over a period of time (e.g., between two time points, three time points, ten time points, etc.). In such embodiments, a change in expression level for a neuroligin biomarker (e.g., NLGN-4Y) over a period of time indicates, for example, an increased risk for developing a prostate disorder, or a change in status for a subject already diagnosed with a prostate disorder. In such embodiments, a change in expression level for a neuroligin biomarker (e.g., NLGN-4Y) over a period of time indicates, for example, a decreased risk for developing a prostate disorder, or an improved status for a subject already diagnosed with a prostate disorder. In some embodiments, comparing expression of neuroligin biomarkers (e.g., NLGN-4Y) over a period of time may be used to test the efficacy of a treatment (e.g., drugs directed toward treating prostate disorders) and/or may be used to test the efficacy of a new form of treatment (e.g., new drugs directed toward treating prostate disorders).

In some embodiments, detection of the presence or absence of a prostate disorder or the characterization of a prostate disorder is accomplished through comparing expression levels of neuroligin biomarkers (e.g., NLGN-4Y) to established thresholds. For example, in some embodiments, a subject's expression level for a neuroligin biomarker detection of the presence or absence of a prostate disorder or the characterization of a prostate disorder is accomplished through comparing expression levels of neuroligin biomarkers (e.g., NLGN-4Y) compared with established neuroligin biomarker threshold levels (e.g., established threshold level for low risk for developing prostate disorder; established threshold level for medium risk for developing prostate disorder; established threshold level for high risk for developing prostate disorder; established threshold level for having prostate disorder versus not having prostate disorder; established threshold level for prostate epithelial cell proliferation; established threshold level for prostate epithelial cell metastasis). Established threshold levels may be generated from any number of sources, including but not limited to, groups of men having prostate disorders, groups of men not having prostate disorders, groups of men having prostate cancer, groups of men having prostate cancer and epithelial cell proliferation, groups of men having prostate cancer and prostate epithelial cell metastasis, groups of men having BPH, groups of men under 35 years of age, groups of men under 50 years of age, groups of men under 70 years of age, groups of men over 65 years of age, groups of men having a prostate disorder and a particular form of treatment, etc. Any number of men within a group may be used to generate an established threshold (e.g., 5 men, 10 men, 20, 30, 50, 500, 5000, 10,000, etc.). Threshold levels may be generated with any type or source of bodily sample from a subject (e.g., including but not limited to, plasma, serum, whole blood, CSF, mucus, and urine).

The information provided through detection of the biomarkers (e.g., NLGN-4Y) can also be used to direct a course of treatment. For example, other agents (e.g., anti-cancer agents) can be administered to subjects that display particular levels of the biomarkers (e.g., NLGN-4Y) of the present invention.

The present invention is not limited to the biomarkers described above. Any suitable marker that correlates with a prostate disorder or the progression of a prostate disorder may be utilized in combination with those of the present invention. For example, in some embodiments, biomarkers identified as being up or down-regulated in prostate cancer using the methods of the present invention are further characterized using microarray (e.g., nucleic acid or tissue microarray), immunohistochemistry, Northern blot analysis, siRNA or antisense RNA inhibition, mutation analysis, investigation of expression with clinical outcome, as well as other methods disclosed herein. Examples of suitable markers include, but are not limited to, neuroligin biomarkers (e.g., NLGN-4Y), and pathway related compounds.

In some preferred embodiments, detection of neuroligin biomarkers (e.g., including but not limited to, those disclosed herein) is accomplished, for example, by measuring the levels of neuroligin biomarkers (e.g., NLGN-4Y) in cells and tissue (e.g., prostate cells and tissues). For example, in some embodiments, NLGN-4Y can be monitored using antibodies. In some embodiments, detection is performed on cells or tissue after the cells or tissues are removed from the subject. In other embodiments, detection is performed by visualizing the biomarker (e.g., NLGN-4Y) in cells and tissues residing within the subject.

In some embodiments, detection of neuroligin biomarkers (e.g., NLGN-4Y) is accomplished by measuring the accumulation of corresponding mRNA in a tissue sample (e.g., cancerous tissue). mRNA expression may be measured by any suitable method known in the art.

In some embodiments, RNA is detected by Northern blot analysis. Northern blot analysis involves the separation of RNA and hybridization of a complementary labeled probe.

In still further embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In some embodiments, reverse-transcriptase PCR(RT-PCR) is used to detect the expression of RNA (e.g., NLGN-4Y). In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In some embodiments, detection of neuroligin biomarkers (e.g., NLGN-4Y) is accomplished through protein expression. Protein expression may be detected by any suitable method. In some embodiments, proteins are detected by binding of an antibody specific for the protein. The present invention is not limited to a particular antibody. Any antibody (monoclonal or polyclonal) that specifically detects neuroligin biomarkers (e.g., NLGN-4Y) may be utilized. In some embodiments, neuroligin biomarkers (e.g., NLGN-4Y) are detected by immunohistochemistry. In other embodiments, neuroligin biomarkers (e.g., NLGN-4Y) are detected by their binding to an antibody raised against neuroligin biomarkers (e.g., NLGN-4Y). In some embodiments, commercial antibodies directed toward neuroligin biomarkers (e.g., NLGN-4Y) are utilized.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981, 785, 6,159,750, and 5,358,691, each of which is herein incorporated by reference. In some embodiments, the analysis and presentation of results is also automated.

In other embodiments, the immunoassay is as described in U.S. Pat. Nos. 5,599,677 and 5,672,480; each of which is herein incorporated by reference.

III. In Vivo Imaging

In some embodiments, in vivo imaging techniques are used to visualize and quantify the expression of neuroligin biomarkers (e.g., NLGN-4Y) in an animal (e.g., a human or non-human mammal). For example, in some embodiments, neuroligin biomarker mRNA or protein is labeled using a labeled antibody specific for the biomarker. Specifically bound and labeled antibodies can be quantified and detected in an individual using any in vivo imaging method, including, but not limited to, radionuclide imaging, positron emission tomography, computerized axial tomography, X-ray or magnetic resonance imaging method, fluorescence detection, and chemiluminescent detection.

The in vivo imaging methods of the present invention are useful in the research of and the diagnosis of prostate disorders (e.g., PCa, BPH) in cells that contain the biomarkers of the present invention (e.g., localized or metastatic cancerous cells or tissue). In vivo imaging is used to quantify and visualize the presence of a biomarker indicative of a prostate disorder. Such techniques allow for diagnosis without the use of a biopsy. In some embodiments, the in vivo imaging methods of the present invention are useful for providing prognoses to patients (e.g., cancer patients, patients suffering from BPH). For example, the presence of neuroligin biomarkers (e.g., NLGN-4Y) expressed at an amount above a certain threshold may be indicative of a cancer likely or not likely to respond to certain treatments. The in vivo imaging methods of the present invention can further be used to detect replicating, neoplastic cells in other parts of the body (e.g., in lymph nodes).

In some embodiments, reagents (e.g., antibodies) specific for the biomarkers of the present invention are fluorescently labeled. The labeled antibodies can be introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 (1990) have described an optimized antibody-chelator for the radioimmunoscintographic imaging of tumors using Indium-111 as the label. Griffin et al., (J Clin One 9:631-640 (1991)) have described the use of this agent in detecting tumors in patients suspected of having recurrent colorectal cancer. The use of similar agents with paramagnetic ions as labels for magnetic resonance imaging is known in the art (See, e.g., Lauffer, Magnetic Resonance in Medicine 22:339-342 (1991)). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111

(3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 (1980)) for In-111 and Tc-99m, and by Scheinberg et al. (Science 215:1511 (1982)). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 (1982)) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 (1978)) for plasma protein, and recently applied successfully by Wong et al. (J. Nucl. Med., 23:229 (1981)) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific biomarker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a biomarker of the present invention). When active, it leads to a reaction that emits light. A CCD camera and software can be used to capture the image and analyze it.

IV. Antibodies

The present invention provides isolated antibodies. In preferred embodiments, the present invention provides monoclonal antibodies that specifically bind to the neuroligin biomarkers (e.g., NLGN-4Y). An antibody against a biomarker of the present invention may be any monoclonal or polyclonal antibody, as long as it can recognize the biomarker. Antibodies can be produced by using a biomarker of the present invention as the antigen according to a conventional antibody or antiserum preparation process.

V. Therapeutics

The present invention provides methods for treating or researching prostate disorders comprising altering (e.g., reducing, inhibiting) NLGN-4Y expression and/or activity. In some embodiments, altering NLGN-4Y expression and/or activity comprises providing to the cell a composition comprising a NLGN-4Y inhibitor or a compound that indirectly reduces NLGN-4Y expression or activity. In some embodiments, altering NLGN-4Y activity comprises altering (e.g., reducing, inhibiting) components of the pathways associated with NLGN-4Y. In some embodiments, altering NLGN-4Y activity comprises altering (e.g., reducing, inhibiting) genes upregulated or downregulated in response to NLGN-4Y expression. In some embodiments, altering NLGN-4Y activity involves a combination of several approaches, including but not limited to, altering NLGN-4Y activity, altering NLGN-4Y associated pathways, and/or altering transcription of upregulated and/or downregulated in response to NLGN-4Y expression.

The present invention is not limited by the type of inhibitor used to inhibit NLGN-4Y activity and/or expression for treating a prostate disorder in a cell. Indeed, any compound, pharmaceutical, small molecule or agent (e.g., antibody, protein or portion thereof) that can alter NLGN-4Y expression and/or activity is contemplated to be useful in the methods of the present invention.

VI. Drug Screening

In some embodiments, the present invention provides drug screening assays (e.g., to screen for new drugs for treating prostate disorders). The screening methods of the present invention utilize neuroligin biomarkers (e.g., NLGN-4Y) identified using the methods of the present invention. For example, in some embodiments, the present invention provides methods of screening for compounds that alter (e.g., increase or decrease), directly or indirectly, the presence of neuroligin biomarkers (e.g., NLGN-4Y). In some embodiments, candidate compounds are antisense agents (e.g., siRNAs, oligonucleotides, etc.) directed against NLGN-4Y, or pathways associated with NLGN-4Y. In other embodiments, candidate compounds are antibodies that specifically bind to a neuroligin biomarker (e.g., NLGN-4Y) of the present invention. Also contemplated to be discoverable using the compositions and methods of the present invention are proteins, peptides, peptide mimetics, small molecules and other agents that can be used to treat prostate cancer.

VII. Kits

In yet other embodiments, the present invention provides kits for the detection, characterization, and/or treatment of prostate disorders (e.g., PCa, BPH). In some embodiments, the kits contain antibodies specific for neuroligin biomarkers (e.g., NLGN-4Y). In some embodiments, the kits further contain detection reagents and buffers. In other embodiments, the kits contain reagents specific for the detection of nucleic acids (e.g., DNA, RNA, mRNA or cDNA, oligonucleotide probes or primers). In preferred embodiments, the kits contain all of the components necessary and/or sufficient to perform a detection assay, including all controls, directions for performing assays, and any necessary software for analysis and presentation of results.

EXAMPLES

The following examples are provided in order to demonstrate and further illustrate certain preferred embodiments and aspects of the present invention and are not to be construed as limiting the scope thereof.

Example I

This example shows the expression pattern for NLGN4 for disorders associated with the prostate. Experiments were conducted on prostate tissue (e.g., benign prostatic hyperplasia tissue, prostatic intraepithelial neoplasia tissue, prostate cancer tissue) to characterize the NLGN4 expression within such disorders. The Gleason score represents a histological scoring system for PSA, wherein a score of 1 designates well-differentiated cells and a score of 5 designates poorly differentiated cells. The higher the score, the more advanced the cancer (Gleason, 1966, Cancer Chemother. Rep. 50:125; Gleason, 1992, Hum. Pathol. 23:273, incorporated herein by reference in their entireties))(BPH: benign prostatic hyperplasia, PIN:prostatic intraepithelial neoplasia, CaP:prostate cancer). Table 1 and FIG. 1 show that the staining (range of 0-3; 0=no staining, 3=strong staining) of the prostate tissue for NLGN-4Y increased with prostate cancer progression, and was lower for non-cancerous prostatic disorder (e.g., benign prostatic hyperplasia tissue in comparison to prostatic cancer tissue).

TABLE 1

Mean degree if staining (range 0-3, 0 = no staining, 3 = strong staining)

| | | |
|---|---|---|
| BPH (n = 120) | 1.25 | |
| PIN (n = 19) | 1.71 | (p = 0.026) vs. BPH, 2 tailed t-test |
| CaP Gleason's 3 (n = 52) | 1.88 | (p = 0.000004) vs. BPH |
| CaP Gleason's 4 (n = 23) | 2.28 | (p = 0.000001) vs. BPH |
| All CaP (n = 75) | 2.00 | (p = 0.000000001) vs. BPH |

Figure 2:
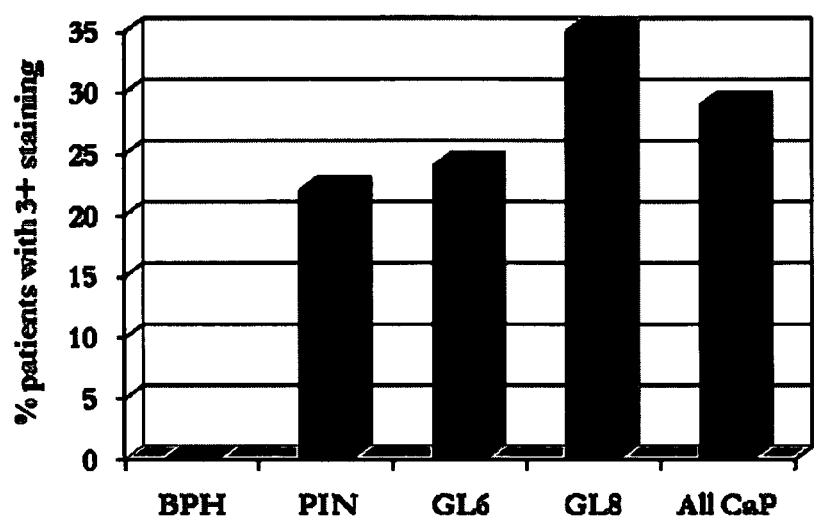
FIG. 2 shows the percent (%) of cells exhibiting moderate (3+) NLGN-4Y staining.

Table 2 and FIG. 2 demonstrate the percent (%) of cells that exhibited moderate (3+) staining for NLGN-4Y. As seen, as prostate tissue progressed, the level of moderate staining increased.

TABLE 2

| % of specimens with 3+ staining | |
|---|---|
| BPH | 0% |
| PIN | 20% |
| CaP Gleason's 3 | 19% |
| CaP Gleason's 4 | 48% |
| All CaP | 28% |

Staining patterns for NLGN-4Y also change between the various types of prostate cancer. For example, Table 3 demonstrates that the type of staining pattern (diffuse, focal, or no staining) differed between different types of prostate cancer.

TABLE 3

| | Staining patterns (%) | | |
|---|---|---|---|
| | Diffuse | Focal | No staining |
| BPH | 80 | 11 | 9 |
| PIN | 100 | | |
| CaP Gleason's 3 | 92 | 2 | 6 |
| CaP Gleason's 4 | 91 | 4 | 4 |
| All CaP | 92 | 3 | 5 |

FIG. 3 shows a Western Blot demonstrating that NLGN-4Y was differentially expressed in a normal prostate cell line, BPH cell line, and prostate cancer cell lines, and that the intensity of expression was higher for the prostate cancer cell lines in comparison to the non-cancerous cell lines.

FIG. 4 shows immunofluorescence staining of NLGN-4Y in BPH and prostate cancer tissue. As shown, immunofluorescence staining of NLGN-4Y was greater in prostate cancer tissue in comparison to BPH tissue.

Figure 5:
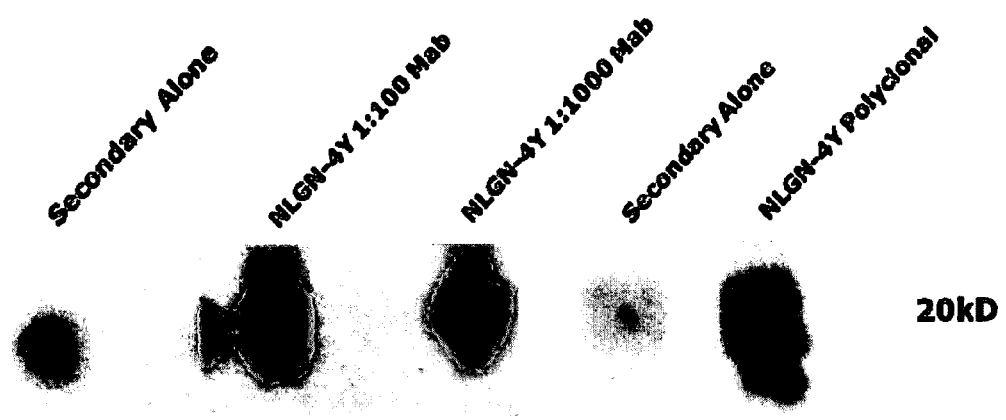
FIG. 5 shows a Western Blot analysis of human serum from a patient with Gleason 9 prostate cancer for NLGN-4Y.

FIG. 5 shows a Western Blot analysis of human serum from a patient with Gleason 9 prostate cancer for NLGN-4Y. As shown, monoclonal and polyclonal NLGN-4Y antibodies show the presence of NLGN-4Y in the human serum.

Example II

This example describes techniques for detecting NLGN-4Y in a human serum sample. The present invention is not limited to this particular technique.

Optimization of ELISA for Serum Samples

Prepare Coating-Reagent Dilutions

1. Place four 17·100-mm test tubes in a rack and add 6 ml PBSN to the last three tubes. In tube 1, prepare a 12-ml solution of coating Neuroligin-4Y antibody at 10 µg/ml in PBSN. Transfer 6 ml of tube 1 solution to tube 2. Mix by pipetting up and down five times. Repeat this transfer and mix for tubes 3 and 4; the tubes now contain the coating reagent at 10, 5, 2.5, and 1.25 µg/ml.
2. Using a multichannel pipet, dispense 50 µl of the coating reagent solutions into wells of four Immulon microtiter plates (i.e., each plate is filled with one of the four dilutions). Incubate overnight at room temperature or 2 hr at 37° C.
3. Fill each well with blocking buffer dispensed as a stream from a squirt bottle and incubate 30 min at room temperature. Rinse plate three times in water. After the last rinse, remove residual liquid by wrapping each plate in a large paper tissue and gently flicking it face down onto several paper towels laying on the benchtop.

Prepare Human Serum Dilutions

4. Place five 12·75-mm test tubes in a rack and add 3 ml blocking buffer to the last four tubes. In tube 1, prepare a 4-ml solution of NLGN-4Y protein standard at 200 ng/ml in PBSN. Transfer 1 ml of tube 1 solution to tube 2. Pipet up and down five times. Repeat this transfer and mix for tubes 3 to 5; the tubes now contain NLGN-4Y protein standard at 200, 50, 12.5, 3.125, and 0.78 ng/ml. If possible, prepare and test serial dilutions of a nonreactive heterologous form of the secondary reactant in parallel.
5. Dispense 50 µl of the NLGN-4Y protein standard solutions into the first five columns of all four coated plates. The most dilute solution is dispensed into column 5, while solutions of increasing concentration are added successively into columns 4, 3, 2, and 1. Thus, the fifth column contains 0.78 ng/ml and the first column 200 ng/ml. Incubate 2 hr at room temperature.
6. Rinse plate three times in water. Fill each well with blocking buffer, vortex, and incubate 10 min at room temperature. Rinse three times in water. After the final rinse, remove residual liquid.

Prepare Developing-Reagent Dilutions

7. Place five 17·100-mm test tubes in a rack and add 3 ml blocking buffer to the last four tubes. In tube 1, prepare a 6-ml solution of developing reagent at 500 ng/ml in blocking buffer. Transfer 3 ml of tube 1 solution into tube 2 and mix. Repeat this transfer and mixing for tubes 3 and 4—the tubes now contain the developing reagent at 500, 250, 125, 62.5, and 31.25 ng/ml.
8. Dispense 50 µl of the developing reagent solutions into the wells of rows 2 to 6 of each plate, dispensing the most dilute solution into row 6 and solutions of increasing concentration successively into rows 5, 4, 3, and 2. Incubate 2 hr at room temperature.
9. Rinse plate three times in water. Fill each well with blocking buffer, vortex, and incubate 10 min at room temperature. Rinse three times in water. After the final rinse, remove residual liquid.

Measure Hydrolysis

10. Add 75 µl MUP or NPP substrate solution to each well, incubate 1 hr at room temperature, and measure the degree of hydrolysis visually or with a microtiter plate reader. An appropriate assay configuration results in 0.50 absorbance units/hr at 405 nm when using NPP as a substrate or 1000 to 1500 fluorescence units/hr when using MUP as a substrate.

Antibody-sandwich ELISA to detect NLGN-4Y

1. Prepare the Neuroligin-4Y capture antibody by diluting specific antibody or immunoglobulin fraction in PBSN to a final concentration of 0.2 to 10 μg/ml.
2. Determine the concentration of Neuroligin-4Y capture antibody and conjugate necessary to detect the desired concentration of antigen by criss-cross serial dilution analysis. Prepare a Neuroligin-4Y capture antibody solution in PBSN at this concentration.
3. Coat wells of an Immulon plate with Neuroligin-4Y capture-antibody solution.
4. Fill each well with blocking buffer dispensed as a stream from a squirt bottle and incubate 30 min at room temperature. Rinse plate three times in water. After the last rinse, remove residual liquid by wrapping each plate in a large paper tissue and gently flicking it face down onto several paper towels laying on the benchtop.
5. Prepare a standard Neuroligin-4Y protein-dilution series by successive 1:3 dilutions of the human serum in blocking buffer.
6. Prepare dilutions of human serum solutions in blocking buffer.
7. Add 50-μl aliquots of the standard Neuroligin-4Y protein-dilutionsolutions and the human serum dilutions to the antibody-coated wells and incubate 72 hr at room temperature.
8. Rinse plate three times in water. Fill each well with blocking buffer, vortex, and incubate 10 min at room temperature. Rinse three times in water. After the final rinse, remove residual liquid.
9. Add 50-μl specific Neuroligin-4Y antibody-alkaline phosphatase conjugate and incubate 2 hr at room temperature.
10. Rinse plate three times in water. Fill each well with blocking buffer, vortex, and incubate 10 min at room temperature. Rinse three times in water. After the final rinse, remove residual liquid.
11. Add 75-μl of MUP or NPP substrate solution to each well and incubate 1 hr at room temperature.
12. Read the plate on a microtiter plate reader.
13. Prepare a standard curve constructed from the data produced by serial dilutions of the standard Neuroligin-4Y protein. Plot antigen concentration on the x axis which is a log scale, and fluorescence or absorbance on the y axis which is a linear scale.
14. Interpolate the concentration of NLGN-4Y protein in the test solutions from a standard curve.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for characterizing prostate cancer tissue in a subject, comprising:
    a) providing a sample from a subject suspected of having prostate cancer;
    b) quantifying expression of NLGN-4Y in said sample; and
    c) characterizing the stage or type of prostate cancer in said prostate tissue sample based on the level of said expression of NLGN-4Y in said sample.

2. The method of claim 1, wherein said quantifying expression of NLGN-4Y comprises quantifying NLGN-4Y mRNA.

3. The method of claim 1, wherein said quantifying expression of NLGN-4Y comprises quantifying a NLGN-4Y polypeptide.

4. The method of claim 3, wherein said quantifying a NLGN-4Y polypeptide comprises exposing said NLGN-4Y polypeptide to an antibody specific to said NLGN-4Y polypeptide and detecting the binding of said antibody to said NLGN-4Y polypeptide.

5. The method of claim 1, wherein said subject comprises a human subject.

6. The method of claim 1, wherein said sample comprises tumor tissue.

7. The method of claim 1, wherein said sample comprises a blood or blood component.

8. The method of claim 1, wherein said characterizing said prostate tissue comprises differentiating aggressive cancers from non-aggressive cancers.

9. The method of claim 1, further comprising the step of d) providing a prognosis to said subject.

* * * * *